(12) United States Patent
Osorio et al.

(10) Patent No.: US 8,588,898 B1
(45) Date of Patent: Nov. 19, 2013

(54) STIMULATION METHODOLOGIES AND APPARATUS FOR CONTROL OF BRAIN STATES

(75) Inventors: Ivan Osorio, Leawood, KS (US); Naresh C. Bhavaraju, Lawrence, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 641 days.

(21) Appl. No.: 12/456,296

(22) Filed: Jun. 15, 2009

Related U.S. Application Data

(63) Continuation of application No. 11/151,386, filed on Jun. 13, 2005, now Pat. No. 7,551,956, which is a continuation of application No. 10/622,239, filed on Jul. 18, 2003, now Pat. No. 6,934,580.

(60) Provisional application No. 60/397,511, filed on Jul. 20, 2002.

(51) Int. Cl.
*A61B 5/04* (2006.01)
(52) U.S. Cl.
USPC .......................................... 600/544; 600/545
(58) Field of Classification Search
USPC .................................................. 600/544, 545
See application file for complete search history.

(56) References Cited

U.S. PATENT DOCUMENTS

| | | | |
|---|---|---|---|
| 4,094,307 A * | 6/1978 | Young, Jr. | 600/544 |
| 4,215,697 A * | 8/1980 | Demetrescu | 600/544 |
| 4,305,397 A | 12/1981 | Weisbrod et al. | |
| 4,323,079 A * | 4/1982 | Demetrescu | 600/544 |
| 5,782,885 A | 7/1998 | Andersson | |
| 5,938,689 A | 8/1999 | Fischell et al. | |
| 5,995,868 A | 11/1999 | Dorfmeister et al. | |
| 6,016,449 A | 1/2000 | Fischell et al. | |
| 6,061,593 A | 5/2000 | Fischell et al. | |
| 6,066,163 A | 5/2000 | John | |
| 6,128,538 A | 10/2000 | Fischell et al. | |
| 6,128,954 A | 10/2000 | Jiang | |
| 6,134,474 A | 10/2000 | Fischell et al. | |
| 6,161,045 A | 12/2000 | Fischell et al. | |
| 6,304,775 B1 * | 10/2001 | Iasemidis et al. | 600/544 |
| 6,360,122 B1 | 3/2002 | Fischell et al. | |

(Continued)

OTHER PUBLICATIONS

Goddard, G.V. et al., "A Permanent Change in Brain Function Resulting from Daily Electrical Stimulation", Exp Neurol. 25(3):295-330 (1969).

(Continued)

*Primary Examiner* — Navin Natnithithadha

(57) ABSTRACT

A system for accessing the brain of a subject to record and/or stimulate brain stares thereof. The system includes control means, first accessing means having a plurality of contact surfaces configured to operatively connect the control means to the brain of the subject to provide three-dimensional stimulation thereof; second accessing means having a plurality of contact surfaces to operatively connect the control means to the brain of the subject to provide access thereto for the purposes of obtaining three-dimensional recordings of the brain electrical activity of the subject; and a waveform bank containing a plurality of stimulating waveforms. The control means is configured to operatively apply a first at least one of the stimulating waveforms of the waveform bank to the brain of the subject through the first accessing means and to assess acceptability within defined limits, as determined by preset criteria, of the subject's response to the application of the at first least one of the stimulating waveforms.

11 Claims, 8 Drawing Sheets

(56) References Cited

U.S. PATENT DOCUMENTS

| | | | |
|---|---|---|---|
| 6,427,086 B1 | 7/2002 | Fischell et al. | |
| 6,442,421 B1 * | 8/2002 | Le Van Quyen et al. | 600/544 |
| 6,459,936 B2 | 10/2002 | Fischell et al. | |
| 6,463,328 B1 | 10/2002 | John | |
| 6,480,743 B1 | 11/2002 | Kirkpatrick et al. | |
| 6,594,524 B2 * | 7/2003 | Esteller et al. | 607/45 |
| 6,597,954 B1 | 7/2003 | Pless et al. | |
| 6,647,296 B2 | 11/2003 | Fischell et al. | |
| 6,658,287 B1 * | 12/2003 | Litt et al. | 600/544 |
| 6,735,475 B1 * | 5/2004 | Whitehurst et al. | 607/46 |
| 6,788,975 B1 * | 9/2004 | Whitehurst et al. | 607/45 |
| 6,934,580 B1 * | 8/2005 | Osorio et al. | 600/545 |
| 7,146,218 B2 * | 12/2006 | Esteller et al. | 607/45 |
| 7,305,268 B2 * | 12/2007 | Gliner et al. | 607/45 |
| 7,551,956 B2 * | 6/2009 | Osorio et al. | 600/545 |

OTHER PUBLICATIONS

Snead, O. Carter III et al., "Exacerbation of Seizures in Children by Carbamazepine", The New England Journal of Medicine, 313(15):916921 (1985).

Manon-Espaillat, Bernstine et al., "Antiepileptic Drug Intoxication: Factors and Their Significance", Epilepsia, 32(1):96-100 (1991).

Racine, R.J. et al., "Kindling-Induced Potentiation in the Piriform Cortex", Brain Researh, 556:218-225 (1991).

Liang, F. et al., "Stimulus-Dependent Reciprocal Up- and Down Regulation of Glutamic Acid Decarboxylase and Ca/Calmodulin-Dependent Protein Kinase II Gene Expression in Rat Cerebral Cortex", Exp. Brain Research, 110:163-174 (1996).

Osorio, Ivan et al., "Real Time Automated Detection and Quantitative Analysis of Seizures and Short Term Predictions of Clinical Onset", Epilepsia. 39(16):615-627 (1998).

Loiseau, Pierre, "Do Antiepileptic Drugs Exacerbate Seizures?", Epilepsia, 39:2-4 (1998).

Perucca, E. et al., "Antiepileptic Drugs as a Cause of Worsening Seizures", Epilepsia, 39(1):5-17 (1998).

Warren, R. James et al., "Effects of Applied Currents on Spontaneous Epileptiform Activity Induced by Low Calcium in the Rat Hippocampus", Brain Research, 806:186-195 (1998).

Osorio, Ivan et al., "Refractory Idiopathic Absence Status Epilepticus: A Probable Paradoxical Effect of Phenyltoin and and Carbamazepine", Epilepsia 41(7):887-894 (2000).

Sunderam, S. et al., "Vagal and Sciatic Nerve Stimulation have Complex Time-Dependent Effects on Chemically Induced Seizures: A Controlled Study", Brain Research 918(1-2): 60-66 (2001).

Osorio, Ivan et al., "An Introduction to Contingent (Closed Loop) Brain Electrical Stimulation for Seizure Blockage, to Ultra-Short Term Clinical Trials and to Multidimensional Statistical Analysis of Therapeutic Efficacy", J. Clin. Neurophysiol. 18(6):533-533 (2001).

Osorio, Ivan et al., "Seizure Blockage With Automated "Closed Loop" Electrical Stimulation: A Pilot Study", Epilepsia 42(7):(Abstract 2.336) (2001).

Vitek, Jerrold L., "Mechanisms of Deep Brain Stimulation: Excitation or Iahibition", Movement Disorders 17(3):S69-S72 (2002).

* cited by examiner

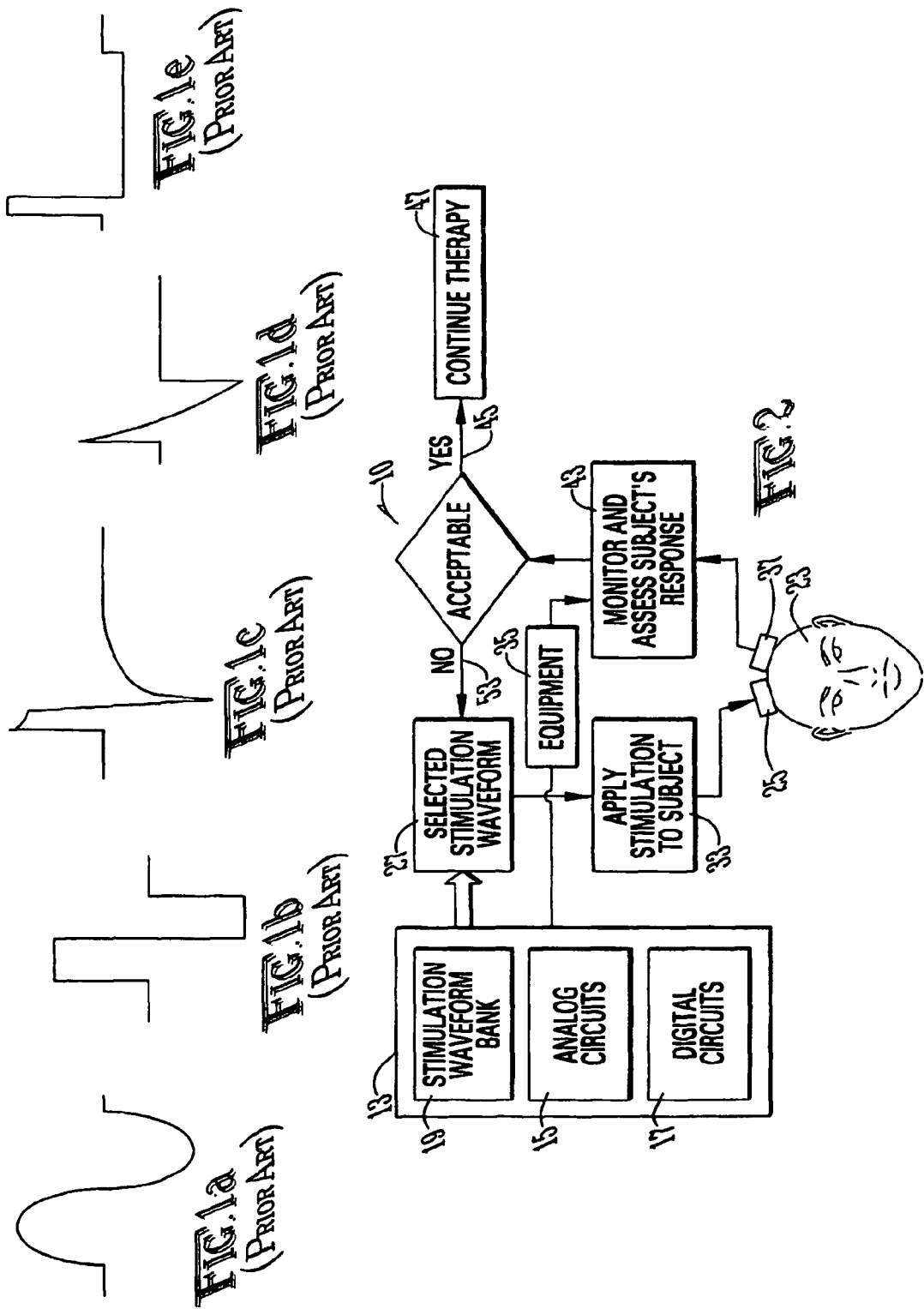

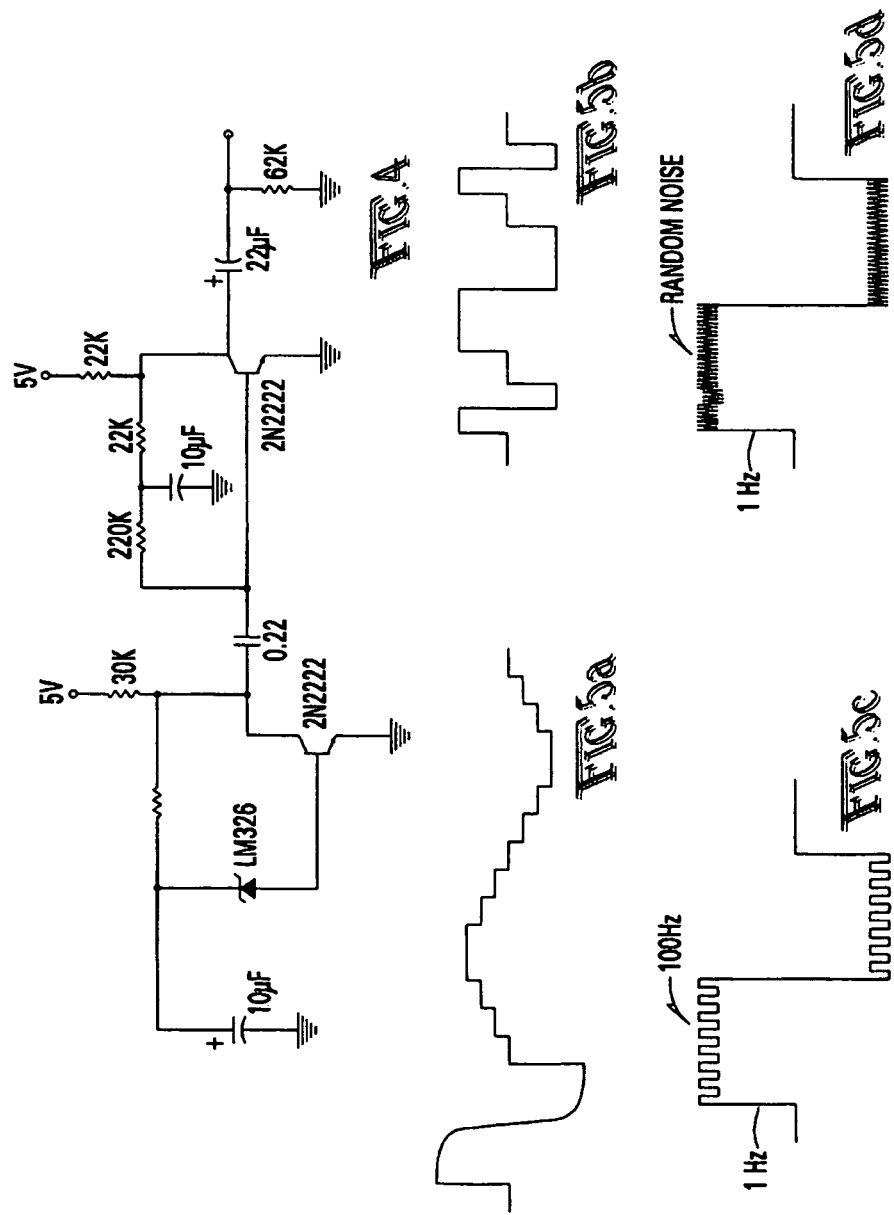

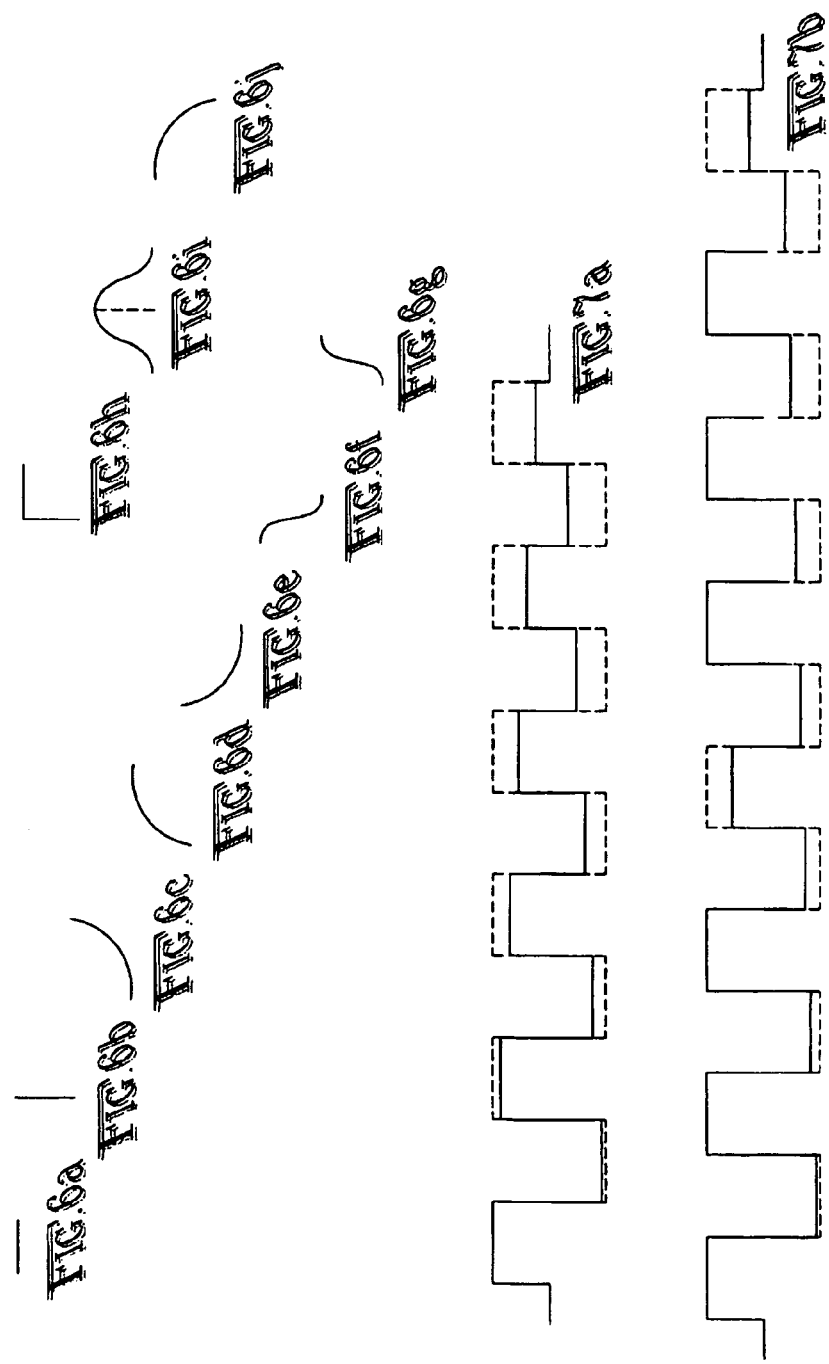

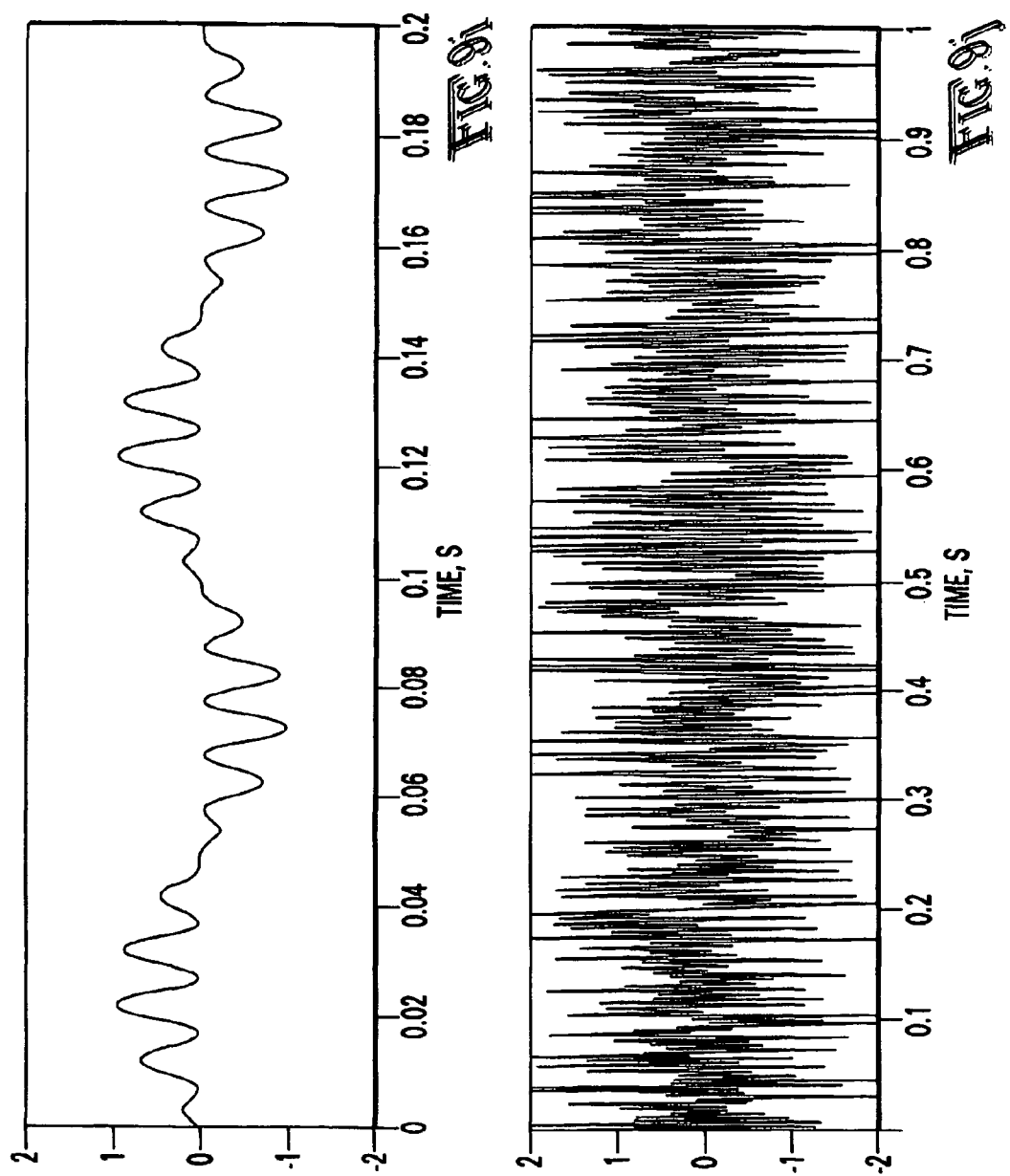

STIMULATION METHODOLOGIES AND APPARATUS FOR CONTROL OF BRAIN STATES

CROSS REFERENCE TO RELATED APPLICATIONS

This application is a continuation of U.S. application Ser. No. 11/151,386 filed Jun. 13, 2005, now U.S. Pat. No. 7,551,956 issued Jun. 23, 2009; which is a continuation application of U.S. application Ser. No. 10/622,239 filed Jul. 18, 2003, now U.S. Pat. No. 6,934,580 issued Aug. 23, 2005; which claims priority of Provisional Patent Application No. 60/397,511 filed Jul. 20, 2002 and entitled "Self-anchoring, Unitized, Mesoelectrode with Multisite, Multimodal Dual (Recording and Control) Capabilities and a Method for Contingent Random, Nonrandom, Turbulent, or Nonturbulent Stimulation for Seizure Blockage."

BACKGROUND OF THE INVENTION

1. Field of the Invention

This invention relates generally to medical apparatus and, more specifically but without limitation, to a system for interacting with the brain of a subject.

2. Description of Related Art

Brain electrical activity (BEA) is a readily accessible and reliable index of brain state and function. It allows distinction between both normal states, such as wakefulness or sleep and its different substates (such as NREM and REM), and abnormal states, such as the ictal and inter-ictal substates of an epileptic brain. BEA is also an important tool for localizing an anatomical substrate of a particular physiological function and for understanding how the function correlates with, or is integrated into, behavior. BEA plays a critical role in the evaluation and treatment of pharmaco-resistant, or intractable, epilepsy, movement disorders, and other neurological diseases. Furthermore, BEA is the basis for real-time automated detection and prediction of the clinical onset of seizures as disclosed in U.S. Pat. No. 5,995,868 issued Nov. 30, 1999 to Ivan Osorio et al, which is incorporated herein by reference. Output from such real-time automated detection and prediction of the clinical onset of seizures provides the cue for delivery of suitable therapeutic means for automated blockage of seizures by either contingent or closed-loop therapy. Closed loop therapy would benefit a significant number of persons with pharmaco-resistant epilepsy, thereby improving quality of life and decreasing morbidity, mortality, and cost of care associated with epilepsy. In addition to epilepsy, recordings and analysis of BEA also plays an increasingly important role in the diagnosis and control of a wide variety of other brain disorders.

Electrical stimulation of brain tissue for prevention, control or blockage of seizures holds promise as a new therapeutic modality. However, electrical stimulation is also a widely utilized tool for the induction of seizures; well known examples are electro-convulsive therapy for mood disorders and an experimental process known as "kindling," in which repeated delivery of very small currents to an animal's brain eventually results in seizures. Seizure induction or blockage using electrical currents, is multi-factorial depending for instance on the state of excitability of the brain and on the various stimulation parameters such as frequency, intensity and duration, among others. One useful strategy for estimating seizure probability is to assess the degree of excitability of brain tissue. The most common tool to assess this is electrical stimulation; however, since electrical currents can increase or decrease the excitability of brain tissue, they must be used judiciously and with great care to decrease the probability that they would significantly alter excitability in transient or permanent ways, rendering the estimation of seizure probability invalid or superfluous.

Generation of afterdischarges (AD's) to gauge brain excitability, as disclosed in U.S. Pat. No. 6,161,045, issued Dec. 12, 2000 to Robert E. Fischell et al, is possibly the clearest example of an invalid and potentially unsafe use of electrical stimulation. It is invalid because it artificially and markedly alters brain excitability, thus introducing a large bias. The methodology disclosed in therein is a clear illustration, at a macroscopic level, of the Uncertainty Principle: an attempt to measure the state of brain excitability causes large changes therein. It is unsafe because AD's may evolve into seizures and because repeated electrical stimulation of AD's, as required in that teaching, may result in "kindling" which would manifest as an increase in seizure frequency or intensity or as new seizure types through induction of new epileptogenic sites. That is, the reliance of the method disclosed in Fischell et al ('045) on artificially induced AD's may sensitize cortical tissue to generate seizures initially in direct temporal relation to stimulations and eventually independently of electrical stimulation, since their therapy provides for repeated trials of electrical stimulation to induce AD's.

The behavior and properties of brain functions such as degree of excitability, are non-stationary, changing as a function of time, circadian rhythms, attention, activity level and other factors. Exogenous factors such electrical stimulation of sufficient intensity and stimulation to cause afterdischarges AD's are particularly well-suited to alter brain tissue excitability. A rational, safe and fruitful approach is to use non-altering, non-biasing quantifiable indices of inherent brain excitability to deliver electrical stimulation or some other form of therapy in close temporal proximity to the onset of seizures or bursts of epileptiform activity, or during epochs of high probability of seizure occurrence, referred to herein as anticipatory or prophylactic stimulation. More importantly, assessment of brain excitability should not alter, either transiently or permanently, its level or state especially in the direction of excitation, as does elicitation of AD's. The inventive methods disclosed herein to validly assess brain excitability, and to use this information to prevent or block seizures, can be described as follows:

a) Passive: With this method, there is no electrical stimulation or other form of testing. The level of cortical excitability is continuously tracked using appropriate tools. The frequency, duration, intensity and temporo-spatial evolution of endogenous or unprovoked epileptiform or seizure activity are the most reliable and valid indices of degree of brain excitability. Real-time accurate quantification or estimation of these activities may be performed using tools including, but not limited to, tools such as the detection algorithm as disclosed in U.S. Pat. No. 5,995,868, issued Nov. 30, 1999 to Ivan Osorio et al, which Computes the "seizure content" in the signal as a function of time and brain site. The output of said tools may be used to quantify or estimate the probability of state change (i.e., seizure occurrence) over a useful and representative time scale as appropriate (such as minutes, days, or months), depending on (i) each subject and prevailing conditions; (ii) brain excitability and probability of state change of the subject; (iii) circadian variations or other rhythms such as menses (i.e. catamenial epilepsy); and (iv) total sleep time. In the case of epilepsy, the distribution of the seizure content of the brain signal as a function of time, brain site/region and other influences, forms a baseline or control phase. The seizure content is then expressed as a seizure index in terms of the amount of time spent in seizure/unit time, or as any other desired index using measures of central tendencies or other statistical standards, such as probability density functions or other appropriate functions. Significant or meaningful deviations from the baseline (as defined for each individual or condition) may then be used to make decisions regarding timing of delivery of therapy, type of therapy and, in the case of electrical stimulation, intensity, frequency and other relevant parameters. Another approach is to measure inter-seizure (or inter-epileptiform discharge) intervals and use these to develop models to estimate the time of arrival and associated probability of the next seizure and accordingly deliver electrical stimulation or some other form of therapy at times when the probability of the occurrence of a seizure exceeds a pre-determined value. Measurements of seizure or epileptiform activity, as immediately hereinbefore described, may be carried out while the subject is receiving therapy and effects are assessed by comparing indices or probabilities to those observed during the baseline. In the case of electrical stimulation, comparisons of parameters such as waveform (i.e, square waves), intensity (in volts or amperes), frequency, pulse width and duration can be performed to determine efficacy using, for example, seizure index or seizure content of the signal as estimated objectively by application of a detection algorithm and, if appropriate, adjust one or more parameters. This approach increases desired beneficial effects of electrical stimulation or some other form of therapy for seizure blockage while decreasing potentially adverse effects thereof, such as an increase in seizure frequency or induction of new seizure types. Those skilled in the art can appreciate that the probability of seizure occurrence may also be estimated by using the "non-seizure content" of the signal as a function of time, global brain state (i,e., sleep) and site when there is more than one independent potentially epileptogenic site (right vs. left mesial temporal regions for example). It also worth mentioning out that the concepts, methods and tools used to estimate probability of seizure occurrence may be applied to biological state changes in general with appropriate modifications.

Measurement of naturally occurring chemicals or compounds such as calcium ions, calmodulin binding protein, or of neurotransmitters such as GABA or glutamate may be used alone or in conjunction with electrical activity, temperature, etc., to estimate degree of brain excitability and, indirectly, seizure probability. Other factors that may alter brain excitability, such as total sleep time or level of activity for example, may be entered into the analysis to improve estimation of state change (i.e., seizure probability).

b) Active: Ultrasound, Doppler, light pulses (i.e., near infrared) or paired pulse stimulation, which have a negligible probability of inducing AD's, are potentially useful tools to assess degree of brain or cortical excitability. Excitability testing may be performed continuously, periodically, randomly or based on a subject's seizure probability record based on electrical, chemical or other types of signals.

Stimulation Methodologies.

Electrical stimulation is an emerging therapy for seizures even though the dynamics of seizures and epilepsy are still poorly understood. Brain electrical stimulation at frequencies above 100 Hz has a therapeutic effect on tremor and other manifestations of Parkinson's disease in humans. Additional evidence from human and animal applications indicates that beneficial effects may also be obtained from stimulation at higher frequencies. For example, high frequency electrical stimulation of rat cerebral cortex simultaneously up-regulates the expression of glutamic acid decarboxylase, which is the enzyme involved in the synthesis of GABA, which is the main inhibitory brain neurotransmitter, and down-regulates calcium/calmodulin dependent protein kinase II expression, which enhances neuronal excitability. The net effect of these changes is to decrease cortical excitability and with it the probability of seizure generation. Charged-balanced square-wave pulses above 100 Hz, delivered in response to automated seizure detections using a validated algorithm, see Osorio et al ('868), decrease seizure frequency, intensity or duration in humans without causing adverse effects. Furthermore, unlike stimulation at 50-60 Hz, the higher frequencies elicit after-discharges only very infrequently, which suggests they do not excite brain tissue. However, there is also preliminary evidence that low frequency stimulation (~1 Hz) reduces the probability of seizure generation.

Frequency (f) of stimulation is only one of several parameters that may shape the direction of a response (excitation vs. inhibition or depression) of nervous tissue. Other parameters are: duration of stimulation (t), intensity (I), pulse width (p), waveform (w), slopes (S) of the rising and descending components of the pulse, polarity (P) of the initial phase of the pulse, and orientation of the electrical field (O) in reference to the epileptogenic site.

U.S. Pat. No. 5,938,689, issued Aug. 17, 1999 to Robert E. Fischell et al, is an example of a prior art implantable electrical stimulation system for the treatment of neurological disorders such as epilepsy or migraine based on the concept of generation of a "current curtain" to contain abnormal brain activity, which has several important limitations:

(a) The degree of spatial and temporal resolution required to generate a "current curtain" to contain seizure spread is unattainable as recording or sensing is done from the cortical surface from where precise localization of seizure onset is not possible. For a further discussion of the limitations of recording BEA only from the cortical surface, see U.S. Pat. No. 7,006,859 entitled "Unitized Electrode with Three-Dimensional Multi-Site, Multi-Modal Capabilities for Detection and Control of Brain State Changes";

(ii) Given the limited spatial resolution of the Fischell et al method, the probability that the tissue, which generates spontaneous seizures, overlaps or is fully congruous with the tissue that is excited to generate after-discharges as required for efficacy, is low. The limited spatial resolution is further compounded by the fact that Fischell et al teaches the use of separate detection and stimulation electrodes which, although not taught by that reference, must be perfectly aligned in the radial direction to avoid unnecessary impairment of temporal resolution with resultant undesired delay of detection and intervention. The end result is that electrical stimulation as taught by Fischell et al is unlikely to be delivered to the seizure onset site with the degree of precision required to be efficacious and the built-in delay between detection and stimulation may be such that the proposed "curtain" of electrical current, even if effective which is unlikely, will not be set in a timely manner. Therefore, the validity of the premise upon which the Fischell et al method rests, is questionable; and (ii) certain histological and electrical properties of brain tissue make the concept of "curtain" for control of epileptic seizures not reducible to practice. For example, brain tissue is neither homogeneous nor isotropic, which is likely to result in unevenness in current density, direction and velocity of formation of the "curtain," which may allow passage of seizure activity into surrounding tissue. Also, due to the anisotropy of brain tissue, the axis of polarization is unlikely to be uniform or have the same orientation for all stimulated tissue, a factor that decreases efficacy since the orientation of this axis in relation to the anatomical orientation of the neuropil determines the degree or extent of the effect on neuronal activity.

(b) The teachings of Fischell et al. ('689) are based on the idea of creating a sheet current of enough intensity to depolarize the neurons so that they form a rigid boundary of any epileptic activity. Without the existence of a closed boundary around the estimated location of the focus, this is practically impossible because it needs the presence of unrealistically large implanted electrodes.

(c) The cortex contains both excitatory and inhibitory neurons. The "curtain," if effective, will not only encompass excitatory but also inhibitory interneurons which, if "blocked," will facilitate spread of seizures by decreasing "surround inhibition," a paradox apparently not addressed or recognized in the Fischell et al teachings.

(d) According to Fischell et al. ('689), the electrical field density drops as a function of distance from the "curtain." As a result, the membrane potential of neurons enveloped by the "curtain" will be depolarized at different levels in reference to their threshold for generating action potentials. One consequence of such electrical inhomogeneity is that neurons at the outer edges may have sub-threshold depolarization, leading to the well-known phenomenon of facilitation which, instead of decreasing, will increase seizure spread. The spread may be directed to other cortical regions or to subcortical structures, such as the thalamus, setting up cortico-thalamo-cortical volleys which may increase cortical excitability and facilitate undesired secondary generalization of focal seizures.

(e) Fischell et al '689 does not teach which electrode is connected positively (+) and which is connected negatively (−), which can be a critical factor in determining direction and extent of current flow and field geometry, which determines efficacy. It is known that depolarization occurs below the cathode first. Thus, making the deeper electrode positive will delay the formation of the "curtain" and may result in seizure spread beyond the "curtain." Hence details on the polarities are an important part of utilizing such a device.

(f) The current density in brain tissue is not uniform along the path of the current flow and hence the path is not a straight line. For example, the current density is highest near the electrodes in case of bipolar stimulation. Consequently, formation of a "curtain" of depolarization is difficult to attain and impossible to be certain as to its location. While the "shape" of an epileptic "focus" is not known, it is highly unlikely that it can be described by straight lines as suggested by Fischell et al ('689). In addition, that reference does not teach: (i) critically important parameters such as duration of the "curtain" required to block and prevent recurrence; nor (ii) how to depolarize in a "sheet-like" manner, rather than in bulk, the involved tissue. The incomplete understanding exhibited in Fischell et al '689 is underscored by statements therein, such as: "As shown in FIGS. 4A, 4B and 4C each electrode could be within or outside the boundary 14 of an epileptic focus, or the electrode could be placed exactly on the boundary 14" (column 4, lines 33-36). Precise delineation of an "epileptic focus" is not possible using electrodes and methods as described therein. Furthermore, the "boundaries" of an "epileptic focus" are not "fixed" but probably vary as a function of neuronal and network excitability which, in turn, vary across the sleep-wake cycle and as a function of other factors, such as light intensity, level of attention, level of activity, availability of energy substrates, etc. The instability of the "boundaries of the epileptic focus" is further increased by the generation of the after-discharges called for in the teachings of Fischell et al ('045).

(g) The total number of separate electrodes and tracks left by the insertion process in Fischell et al ('689) required for seizure detection and EBS (see column 4, lines 7-11) is more than those required by the teachings herein and those of U.S. Pat. No. 7,006,859 entitled "Unitized Electrode with Three-Dimensional Multi-Site, Multi-Modal Capabilities for Detection and Control of Brain State Changes". The Fischell et al teaching of separate sensing and stimulating units adds unnecessary bulk and processing complexity. The therapeutic ratio of such an arrangement, defined as benefits/adverse effects or therapeutic ratio, appears to be unacceptably low, in light of the spatial incongruence and temporal delay that the Fischell et al approach introduces and the bulk/complexity mentioned immediately hereinbefore.

What is needed is a methodology for automatic and quantitative assessment of cortical excitability using means/methods that do not alter that cortical excitability; a methodology for assessment of cortical excitability using multiple indices such as electrical activity, concentration of chemicals, responses to ultrasound or near-infra-red light, changes in temperature, etc.; a methodology having the ability to automatically quantify the effect of individual electrical stimulation parameters or sets of parameters; a methodology having the ability to automatically remove/delete, add and rank individual parameters or set of parameters according to efficacy; and a methodology having the ability to automatically tailor the response to each subject, taking into account circadian or ultradian variations in cortical excitability, exogenous or endogenous factors which may alter it, etc.

SUMMARY OF THE INVENTION

The present invention discloses methods and apparatus using at least one of the aforementioned parameters (i.e., (f), (t), (I), (p), (w), (S), (P), (O)) and a) tools for automatic multidimensional quantitative seizure analysis (including but not limited to intensity, duration and spatial extent) and of other biological signals such as those obtained for an EKG; b) tools for automatic deterministic or random searches and optimization of therapy; which searches may be performed by using genetic algorithms, genetic programming or neural networks and may be carried out by fixing any or all (i.e., (t) (I), (p), (w), (S), (P), (O)) but one of the parameters (i.e, (f)) and varying this parameter until a beneficial effect is attained, or there are adverse effects, or safety limits are exceeded. Also more than one parameter (i.e., (f) and (t)) may be varied simultaneously and the choice of which parameters are varied (i.e., (f) and (t), or (S) and (P)) and their number (i.e., (f) and (t), or (f), (t) and (I)) may be random or applied according to preset rules; c) with feedback loops to automatically: (i) delete those parameters which increase brain excitability and the probability of seizure occurrence, or are unsafe in any way or not tolerated by the patient as determined by using tools mentioned in (a) or by clinical reports; (ii) to save those parameters which do not cause adverse effects; (iii) rank each saved parameter (i.e, (I), (f), etc) according to efficacy (as measured by using (a)) from highest to lowest; (iv) assemble full sets of parameters and test them (i.e., (f), (t), (I), (p), (w), (S), (P), (O)) based on their efficacy rank; (iv) repeat the steps outlined in c(i), c(ii) and c(iii); d) the ability to automatically track and log parameter or parameter set efficacy and adverse effects as a function of, at least, circadian or ultradian rhythms, level of activity, total sleep time, luminance, body temperature and brain tissue, CSF or serum concentrations of naturally occurring or administered compounds using tools in (a), this being done in light of the possibility that a top ranked parameter or set of parameters for seizures occurring during the daytime may lose efficacy for seizures occurring at night; e) the ability to automatically rank parameters or sets of parameters according to the efficacy as a function of state as described in d); f) the ability to automatically change parameters or sets of parameters according to circadian rhythms, or level of activity, or time of the months (i.e., menstrual period), etc., to increase efficacy and decrease adverse effects; and g) an electrical waveform bank and an electrical waveform component bank from where waves with characteristic shapes can be assembled into trains or components can be assembled into waves and trains thereof for seizure blockage. Selection of waveforms and assemblage into trains or selection of components and assemblage into trains and of waveforms into trains may be performed using deterministic or random searches, genetic algorithms, genetic programming or neural networks, and guided by the output of tools for automatic multidimensional quantitative seizure analysis (including but not limited to intensity, duration and spatial extent) and of other biological signals such as those obtained for an EKG. Any or all operations/functions of this waveform bank may also be performed automatically or selectively.

The improvement of the present invention includes a system for accessing the brain of a subject to record, predict, detect and/or control brain states thereof. The system includes control means, first accessing means having a plurality of contact surfaces configured to operatively connect the control means to the brain of the subject to provide three-dimensional stimulation thereof; second accessing means having a plurality of contact surfaces to operatively connect the control means to the brain of the subject to provide access thereto for the purposes of obtaining three-dimensional recordings of the brain electrical activity of the subject; and a waveform bank containing a plurality of stimulating waveforms. The control means is configured to operatively apply a first at least one of the stimulating waveforms of the waveform bank to the brain of the subject through the first accessing means and to assess acceptability within defined limits, as determined by preset criteria, of the subject's response to the application of the at first least one of the stimulating waveforms.

PRINCIPAL OBJECTS AND ADVANTAGES OF THE INVENTION

The principal objects and advantages of the present invention include providing a methodology for automatic and quantitative assessment of cortical excitability using means/methods that do not alter that cortical excitability; providing such a methodology for assessment of cortical excitability using multiple indices such as electrical activity, concentration of chemicals, responses to ultrasound or near-infra-red light, changes in temperature, etc.; providing such a methodology having the ability to automatically quantify the effect of individual electrical stimulation parameters or sets of parameters; providing such a methodology having the ability to automatically remove/delete, add and rank individual parameters or set of parameters according to efficacy; and providing such a methodology having the ability to automatically tailor the response to each subject, taking into account circadian or ultradian variations in cortical excitability, exogenous or endogenous factors which may alter it, etc.

Other objects and advantages of this invention will become apparent from the following description taken in conjunction with the accompanying drawings wherein are set forth, by way of illustration and example, certain embodiments of this invention.

BRIEF DESCRIPTION OF THE DRAWINGS

FIGS. 1(a)-1(e) depicts typical waveforms utilized by prior art methods.

FIG. 2 presents a schematic and block diagram presenting a method for applying stimulation, according to the present invention.

FIG. 4 depicts a circuit that can be used to generate random noise for stimulation purposes, according to the present invention.

FIGS. 5(a)-5(d) depict examples of hybrid waveform trains containing combinations of different types of stimulation waves, according to the present invention.

FIGS. 6(a)-6(j) depict waveform components that can be combined to generate more complex waveforms for stimulation purposes, according to the present invention.

FIGS. 7(a)-7(b) depict waveforms with delayed charge-balancing, according to the present invention.

FIGS. 9(a)-9(j) depict hybrid waveforms that can be generated and used for stimulation purposes, according to the present invention.

DETAILED DESCRIPTION OF THE PREFERRED EMBODIMENTS

Figure 3A:
FIGS. 3(a)-3(h) depict a bank of stimulation waveforms, according to the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The system of the present invention includes various methodologies or strategies for detection and control of brain states in a subject as hereinafter disclosed. Various waveforms, all charge-balanced, applied by prior art methodologies are depicted in FIGS. 1(a)-1(e), the limitations of which have hereinbefore been described. In other words, prior art waveforms of electrical pulses for therapeutic purposes are few in number (i.e., sinusoidal, triangular, square) (FIG. 1) and are identical to those which have been used for several decades to elicit AD's and seizures.

Features of the stimulation methodology of the present invention can be briefly described as comprising the following:

(a) producing waveform or pulse train hybridization in analog or digital;

(b) means of optimizing in a quantifiable manner the process of delivering such waveforms as stimulating electrical currents to a subject using a multi-pronged unitized electrode as disclosed in U.S. Pat. No. 7,006,859 entitled "Unitized Electrode with Three-Dimensional Multi-Site, Multi-Modal Capabilities for Detection and Control of Brain State Changes", which is incorporated herein by reference, to provide stimulating and recording access to the brain of the subject;

(c) means of controlling parameters such as duration, timing of delivery, etc., in an automated manner; and (d) identifying parameters for electrical stimulation that do not elicit after-discharges or result in increases in seizure content of the signal through the use of quantitative algorithms and using those parameters for closed-loop therapy; change/update parameters automatically in response to variations in brain excitability index or content.

The reference numeral 10 generally refers to a system for detection and control of brain states in a subject in accordance with the present invention, as shown in FIGS. 2 through 9(j). A schematic and block diagram representation of the system 10 of the present invention is presented in FIG. 2. As depicted in FIG. 2, the stimulation waveforms can be selected from a bank and then feedback from a subject's response can be used to switch to different waveforms or to change the parameters of the existing waveform. The system 10 comprises electronic control apparatus 13 including a computer or microprocessor, analog circuits 15 and/or digital circuits 17, and a waveform bank 19. The control apparatus 13 is connected to a subject 23 via a multi-contact unitized electrode 25 having three-dimensional recording and/or stimulating capabilities, such as a unitized electrode 25 as disclosed in U.S. Pat. No. 7,006,859 entitled "Unitized Electrode with Three-Dimensional Multi-Site, Multi-Modal Capabilities for Detection and Control of Brain State Changes";

A stimulation waveform 27 is selected from the waveform bank 19 or generated by the control apparatus 13 as hereinafter described and applied, step 33, to the subject 23 through the electrode 25. Equipment 35 is connected to the subject 23, either through the same unitized electrode 25 or through another multi-contact unitized electrode 37, to monitor and, in conjunction with the control apparatus 13, assess the subject's response, step 43, to the application of the stimulation, step 33. If the control apparatus determines that the response of the subject is acceptable, step 45, application of the stimulation is continued, step 47. If the control apparatus 13 determines that the response of the subject 43 is not acceptable, step 53, application of the originally selected waveform to the subject 23 is discontinued, a different stimulation waveform 27 is selected from the waveform bank 19 or generated by the control apparatus 13 as hereinafter disclosed, and the procedure just described is repeated by applying, step 33, the newly selected waveform to the subject through the electrode 25. This re-selection and re-application procedure is repeated until a waveform is applied to the subject 23 that the control apparatus 13 determines that an acceptable response thereto is elicited from the subject 23.

Figure 3B:
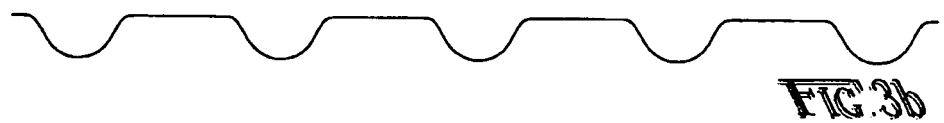
Figure 3C:
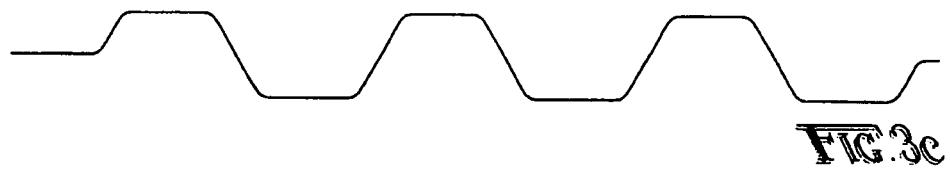
Figure 3D:
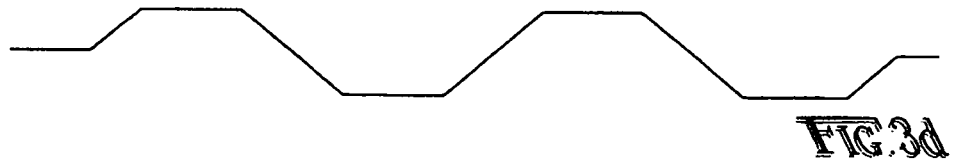
Figure 3E:
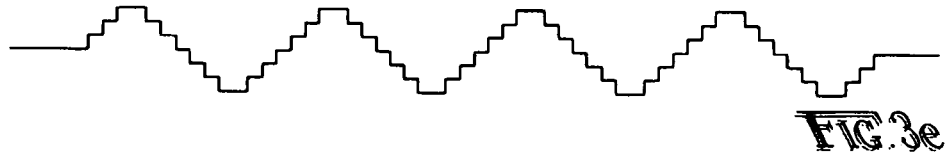
Figure 3F:
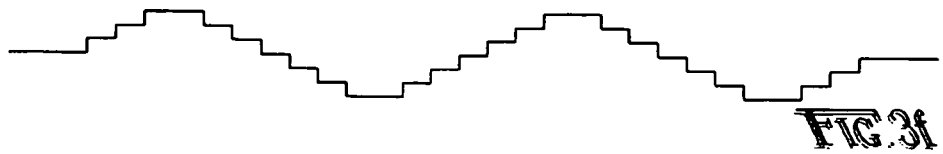
Figure 3G:
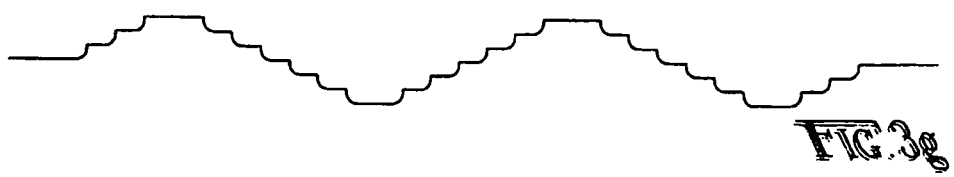
Figure 3H:
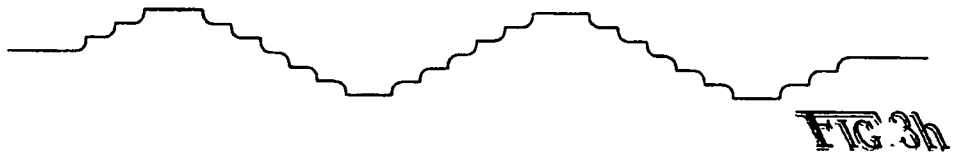

FIG. 3(a) through 3(h) depict various waveforms included in the stimulation waveform bank 19 of the control apparatus 13. FIG. 3(a) depicts a sinusoidal-type waveform with flat peaks and troughs. FIG. 3(b) depicts a waveform with flat peaks with continuously varying troughs therebetween. FIG. 3(c) depicts a waveform similar to the waveform shown in FIG. 3(a) but having a higher frequency. FIG. 3(d) depicts a waveform with flat peaks and troughs with linearly ascending and descending ramps therebetween. FIG. 3(e) depicts a waveform with flat peaks and troughs with ascending and descending steps of equal length therebetween. FIG. 3(f) depicts a waveform with flat peaks and troughs with ascending and descending steps wherein each succeeding step on the left side of a peak is twice the length of the immediately preceding step and the steps on the right side of a peak are a mirror image of the steps on the left side of the peak. FIG. 3(g) depicts a waveform with steps on the left side of a peak having identical slopes that increase exponentially to each succeeding step and the steps on the right side of a peak are a mirror image of the steps on the left side of the peak. FIG. 3(h) depicts a waveform with steps on the left side of a peak having identical slopes that increase exponentially to each succeeding step and the steps on the right side of the peak decrease exponentially to each succeeding step. The various waveforms in the stimulation waveform bank 19 are designed to provide high information content to thereby increase efficacy and expand the scope of applications for control of undesirable brain state changes or state changes of other organs/systems. Those skilled in the art will appreciate that the waveforms disclosed in the preferred embodiment, are a sample of what may be an infinitely large number. Charge-balanced waveforms of any shape and wide range of frequencies (0.001-10,000 Hz, for example) can be generated using appropriate mathematical functions; waveform generation and choice of waveform for therapeutic applications may be deterministic or random. In other words, it is to be understood that stimulation waveforms other than those depicted may also be included in the stimulation waveform bank 19 of the control apparatus 13.

As described herein, waveforms are sequentially automatically or selectively chosen to be applied to a subject for therapeutic purposes, the effect thereof on the subject being assessed statistically. If the effect or degree/level of control (as determined for each subject, or seizure type in the case of epilepsy) is not satisfactory or statistically not significant, that waveform will be replaced by another one, either automatically or selectively, and the procedure repeated until either an efficacious one is found or there are no more waveforms in the bank 19.

A further application of the present invention is to, either automatically or selectively direct the control apparatus 13 to assemble different waveforms from the waveform bank 19 into a hybrid waveform train, as depicted in FIGS. 5(a) and 5(b), and use those hybrid waveform trains for control of brain state changes. FIG. 5(a) depicts a hybrid waveform wherein two waveforms have been joined end-to-end. FIG. 5(b) depicts a hybrid waveform wherein two waveforms are superimposed. Waveforms may be combined in any possible way to form hybrid waveform trains. Waveform selection for hybrid waveforms may be random or deterministic based on feedback from results of stimulation, on fuzzy logic, on searches using genetic algorithms or genetic programming, or on other suitable means of selection. In addition, the control apparatus 13 may have the means to deterministically or randomly and automatically or selectively change stimulation parameters such as intensity, pulse width, polarity, duration of stimulation, timing of delivery in reference to onset of state change or to cycle or phase of waves, inter pulse interval, geometry of stimulation, while maintaining current density at safe levels.

Figure 8C:
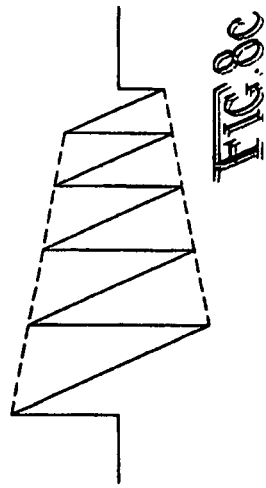
FIGS. 8(a)-8(c) depict sawtooth waveforms that can be used for stimulation purposes, according to the present invention.
Figure 8B:
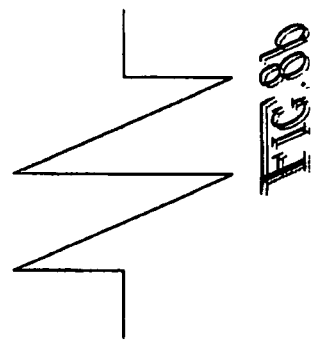
Figure 8A:
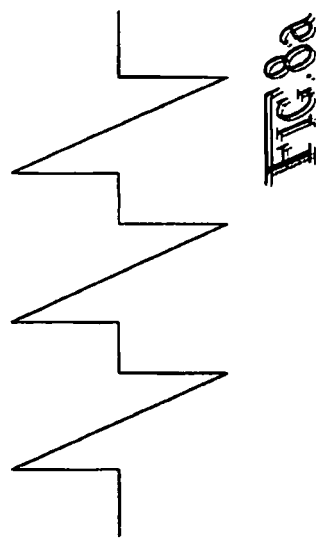

Still further, the bank 19 may also contain waveform components, see FIGS. 6(a) through 6(j), that can be combined and used by the control apparatus 13 to generate waveforms of any desired combination and complexity using either digital technology or analog technology. If desired, the control apparatus 13 may include a digital-to-analog converter to convert digital waveforms to analog waveforms. In addition, the control apparatus 13 can modify any waveform with delayed charge-balancing. For example, FIG. 7(a) depicts a waveform wherein charge-balancing has been delayed by one cycle and with decreasing intensity, and FIG. 7(b) depicts a waveform wherein charge-balancing has been delayed by three cycles and with decreasing intensity. Other waveforms that can be utilized by the present invention include a complex sawtooth waveform depicted in FIG. 8(a), a simple sawtooth waveform depicted in FIG. 8(b), and a sawtooth waveform with delayed charge-balance and decreasing intensity is depicted in FIG. 8(c).

Figure 9A:
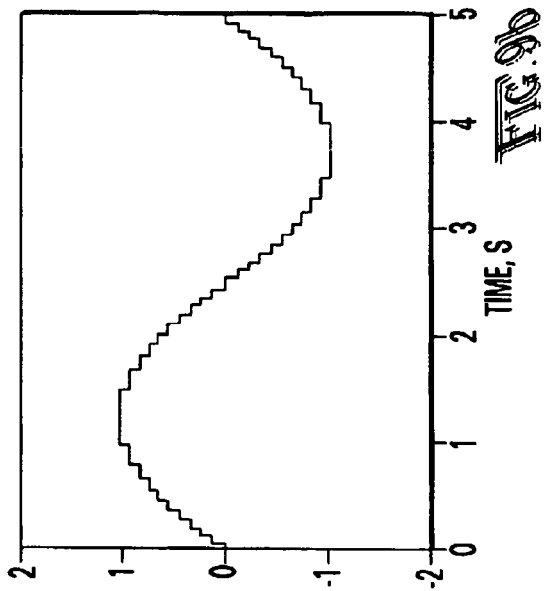
Figure 9B:
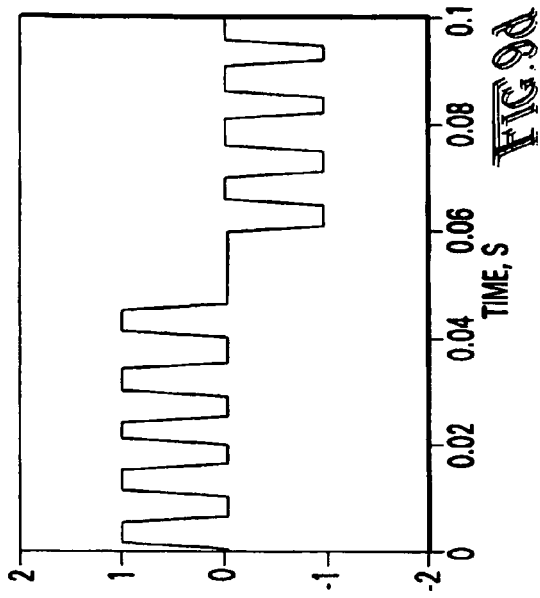
Figure 9C:
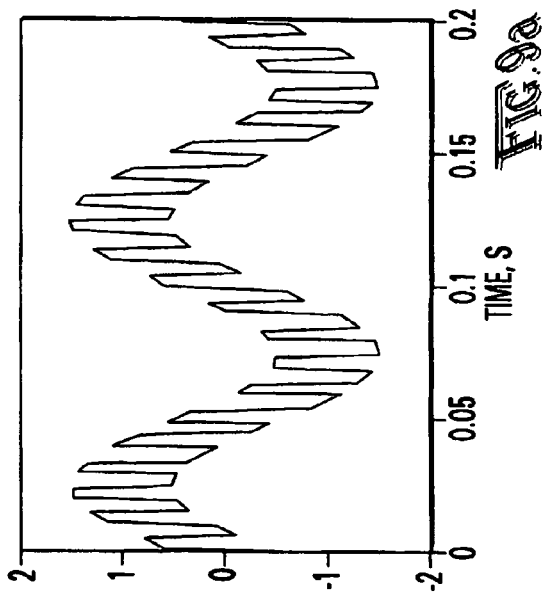
Figure 9D:
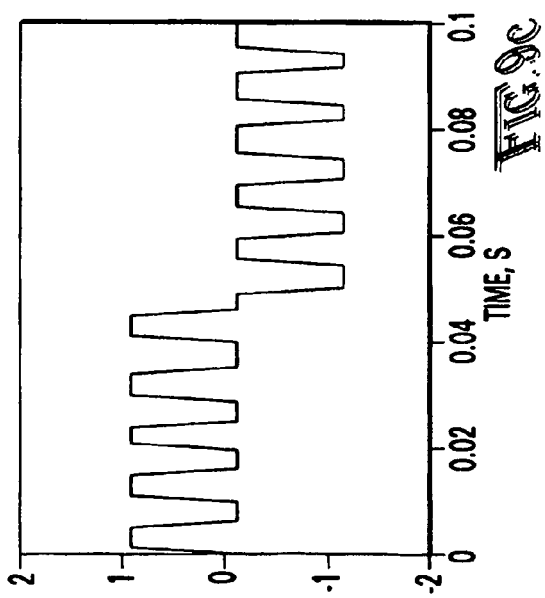
Figure 9E:
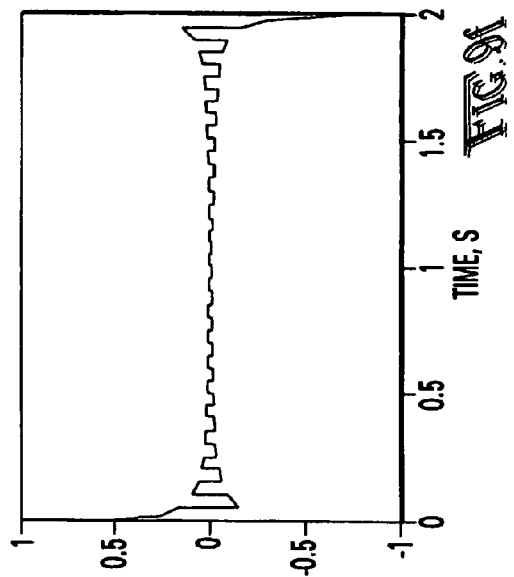
Figure 9F:
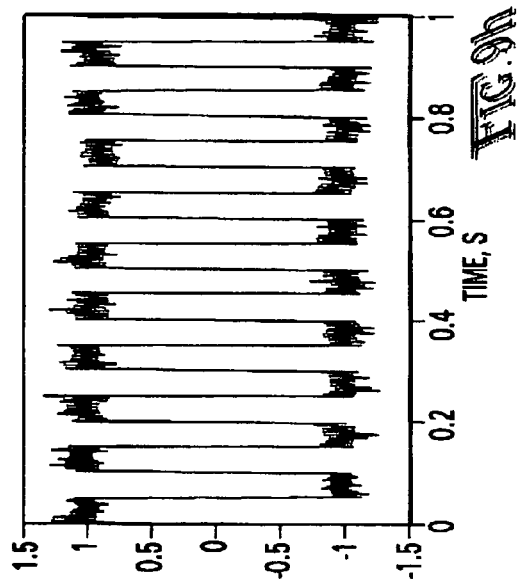
Figure 9G:
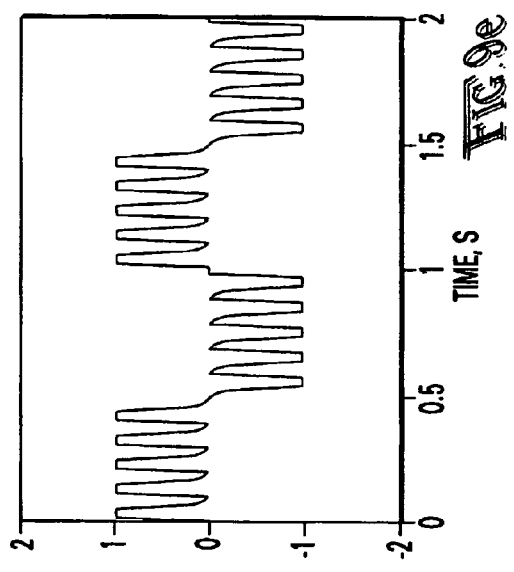
Figure 9H:
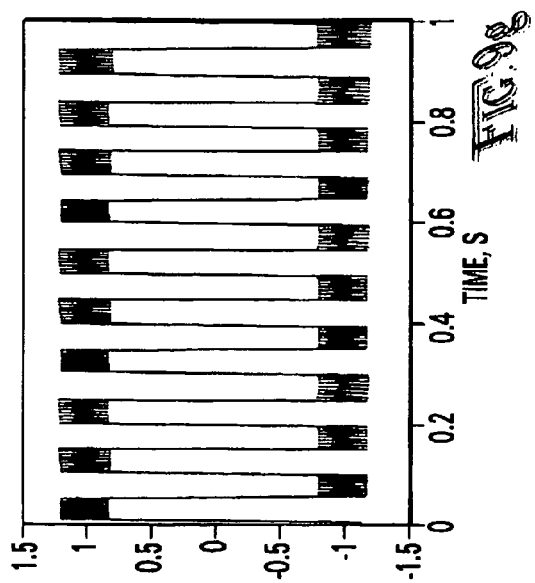

FIGS. 9(a) through 9(i) depicts examples of other hybrid waveforms that can be generated by the control apparatus 13. FIG. 9(a) depicts a hybrid waveform with delayed charge-balancing comprising superimposed sinusoid and square waves. FIG. 9(b) depicts a hybrid waveform comprising a sinusoid with ascending and descending steps. FIG. 9(c) depicts a hybrid waveform comprising hybrid steps with an immediate transition. FIG. 9(d) depicts a hybrid waveform similar to FIG. 9(c) but with a delayed transition. FIG. 9(e) depicts a hybrid waveform comprising superimposed square waves with exponentially decaying falling edges. FIG. 9(f) depicts a hybrid waveform comprising superimposed square waves with delayed charge-balance and having selected exponentially decaying falling edges. FIG. 9(g) depicts a hybrid waveform comprising superimposed square waves with different frequencies. FIG. 9(h) depicts a hybrid waveform comprising a square wave with random noise. FIG. 9(i) depicts a hybrid waveform comprising superimposed sinusoids of different frequencies with delayed charge-balancing.

As aforesaid, FIGS. 9(a)-9(i) depict computer-generated graphs of several hybrid waveforms of the present invention. It is to be understood that other waveforms with different frequencies and amplitudes or other waveforms can be similarly generated by the control apparatus 13 and applied to the subject. There are at least three methods in which these waveforms can be generated by the present invention:

a) One method for generating waveforms by the present invention is to use analytical functions and their combinations to generate a waveform and then use a digital-to-analog converter to output a waveform for stimulation purposes as taught herein. For example, an equation such as V=A sin(2πft) can be used to generate a charge-balanced sinusoidal wave with amplitude, A, and frequency, f. Another example is to generate a random number sequence with the control apparatus 13 and use that sequence to generate a waveform for stimulation. A pseudo-random generator may also be used to generate waveforms. An example of code for generating random noise is provided in the Appendix, attached hereto and incorporated herein by reference.

b) A second method for generating waveforms by the present invention is to store numbers in a table and output the numbers to generate a waveform of any desired shape. This method is useful for generating complicated waveform shapes and repeating them.

c) A third method for generating waveforms by the present invention is to use analog or digital circuits to shape the waveforms. For example, an oscillator (such as an astable multivibrator, crystals, etc.) can be used as a source for generating a stimulation waveform.

The present invention may also include generators of electrical turbulence or random noise for delivery to the region of interest of the subject, using analog or digital technology, see FIG. 9(j), and consisting of random frequencies and random amplitudes that have zero mean. In this type of application, seizures constitute the signal, S, and noise, N, is generated as described herein. FIG. 9(j) depicts an example of normally distributed random noise. This approach is based on a fundamental principle of Information Theory, namely, increases in N, sufficiently above levels normally present in the brain, decrease the signal-to-noise ratio, S/N, thus blocking or attenuating seizures. The random noise or turbulence can be created by using circuits such as that shown in FIG. 4, or by using software to rapidly and randomly change stimulation waveforms in time and space. Spatial turbulence can be achieved by the present invention by switching on and off in a random fashion different channels used in a particular stimulation application. Further, frequency, amplitude and pulse width on the channels can also be changed randomly.

In addition, the present invention may include phase-resetting of bioelectrical oscillations, which is a well-known phenomenon commonly exploited for the treatment of cardiac rhythm abnormalities. Phase-resetting requires direct current pulses (dc-pulses), which are potentially injurious to neurons, because they are not charge-balanced. While phase-resetting of neuronal oscillations has been documented and could be exploited to block seizures, the inability of the prior art to use true dc-pulses in humans limits its clinical applicability. However, near-dc pulses, defined as pulses with long phases in which charge-balancing occurs slowly, may cause phase-resetting without injuring brain tissue. One method wherein the present invention can successfully achieve this is to introduce a dc-bias at the beginning of a pulse or train and to linearly, exponentially or in some other form decrease the magnitude of the dc-bias until its magnitude reaches zero. Another method to decrease the potentially cytotoxic effect of dc-pulses is to decrease pulse width linearly, exponentially or in some other form, or by making intensity and duration inversely related or both. The duration and intensity of the near-dc pulses may also be automatically controlled via feedback from the oscillation under control. Some delayed charge-balanced stimulation waveforms of the present invention are depicted in FIGS. 7(a) and 7(b).

The present invention may also be used for detection and prediction purposes as taught in U.S. Pat. No. 5,995,868 issued Nov. 30, 1999 to Ivan Osorio et al.

It is to be understood that while certain forms of the present invention have been illustrated and described herein, it is not to be limited to the specific forms or arrangement of parts described and shown.

APPENDIX A

Example Code in Matlab for Generation of Some Stimulation Waveforms

```
% StimWaveForms.m
% Examples generated for stimulation waveform bank
% submitted along witht he stimulation methdologies utility patent
% Naresh C. Bhavaraju, Jul. 2, 2003
% Copyright (c) Flint Hills Scientific, LLC
%
=========================================================
dt=0.001;
t=0:dt:1-dt;
a=sin(2*pi*100*t);
b=sin(2*pi*10*t);
% 1: hybrid waveform: sinusoid+square with delayed charge balancing
sq1=sign(a)*0.5;
x=b+sq1;
figure(1);
subplot(2,2,1);plot(t,x)
set(gca,'xlim',[0 0.2]);
set(gca,'ylim',[-2 2]);
title('hybrid waveform: sinusoid+square with delayed charge balancing');
```

```
xlabel('time, s');
% print -dpsc StimWaveforms.ps;
% 2: ascending and descending steps
t=0:dt:5-dt;
c=sin(2*pi*0.2*t);
a1=round(c*10);
a1=a1/10;
subplot(2,2,2);plot(t,a1)
set(gca,'ylim',[-2 2]);
title('Ascending and descending steps');
xlabel('time, s');
% print -dpsc -append StimWaveforms.ps;
% 3: Hybrid steps with immediate transition
dt=0.001;
t=0:dt:0.1-dt;
t1=0:dt:0.05-dt;
t2=0.05:dt:0.1-dt;
a1=sin(2*pi*100*t1);
a2=sin(2*pi*100*t2);
x1=0.5+0.5*sign(a1);
x2=-0.5-0.5*sign(a2);
x=[x1 x2];
y=[x1 zeros(1,10) x2];
subplot(2,2,3); plot(t,x);
set(gca, 'ylim',[-2 2]);
title('Hybrid steps with immediate transition');
subplot(2,2,4); plot([0:length(y)-1]*dt,y);
set(gca, 'ylim',[-2 2]);
title('Hybrid steps with delayed transition');
xlabel('time, s');
% print -dpsc -append StimWaveforms.ps;
% 4: 'Square waves with exponentially decaying falling edges'
figure(2);
t1=[1:50]*0.1;
a=[zeros(1,10) ones(1,40) exp(-t1)];
a1=-fliplr(a);
x=[a a a a a a1 a1 a1 a1 a1];
x=[x x];
t=[0:length(x)-1]*dt;
subplot(2,2,1);plot(t,x);
set(gca, 'ylim',[-2 2]);
title('Square waves with exponentially decaying falling edges');
xlabel('time, s');
% print -dpsc -append StimWaveforms.ps;
%5: Delayed charge balance
t=0:dt:1-dt;
a=sin(2*pi*10*t);
a1=sign(a);
amp=[1:0.1:100.9];
a2=a1./amp;
% plot(a2)
a3=fliplr(a2);
% x=[a2 a3];
% plot(x)
x=[a2-a3];
t1=[0:length(x)-1]/1000;
subplot(2,2,2);plot(t1,x)
title('Delayed chanrge balance');
xlabel('time, s');
% print -dpsc -append StimWaveforms.ps;
%6: Hybrid square wave with two frequencies
a=sin(2*pi*100*t);
b=sin(2*pi*10*t);
b1=sign(b);
a1=sign(a);
a1=a1*0.2;
x=a1+b1;
t1=[0:length(x)-1]/1000;
subplot(2,2,3);plot(t1,x)
title('Hybrid square wave with two frequencies');
xlabel('time, s');
% print -dpsc -append StimWaveforms.ps;
%7 Hybrid square wave with random noise
a1=randn(1,1000);
a1=randn(1,1000)*0.1;
x=a1+b1;
subplot(2,2,4);plot(t1,x);
title('Hybrid square wave with random noise');
xlabel('time, s');
% print -dpsc -append StimWaveforms.ps;
%8: hybrid waveform: sinusoid+square with delayed charge balancing
figure(3);
t=0:dt:1-dt;
a=sin(2*pi*100*t);
b=sin(2*pi*10*t);
x=(0.5+0.5*a).*b;
plot(t,x);
set(gca, 'xlim',[0 0.2]);
set(gca, 'ylim',[-2 2]);
title('hybrid waveform: sinusoid+square with delayed charge balancing');
xlabel('time, s');
% print -dpsc -append StimWaveforms.ps;
```

Example C++ Code for Pseudo Random Noise Generation Using Autoregression

```
fDbyt = fDt/fTau; // parameters for generating autoregression
srand( (unsigned)time( NULL ) ); // initializing the random seed
    double DC_Component;
    DC_Component =0;
    iter = 1;
    dNoise[0] = 0.0; // initial value of the series
    while (iter < m_uNoiseDuration)    //
    {
       dNoise[iter]=(((1-fDbyt) * (dNoise[iter-1] +
       fSig*sqrt(2*fDbyt)*rand( ))))/16;
       DC_Component += dNoise[iter];
       iter++;
    }
    // removing DC component from the noise
    DC_Component /= ( m_uNoiseDuration-1 );
    for(unsigned j =1;j<m_uNoiseDuration;j++)
    {
       dNoise[j] -= DC_Component;
    }
```

What is claimed and desired to be covered by Letters Patent is:

1. A system for controlling a seizure of a subject, the system comprising:
    (a) receiving means structured and configured to monitor and receive three-dimensional signals of a seizure being emitted by a subject's brain;
    (b) a waveform bank structured and configured to deliver an adaptive stimulation waveform or train(s) of waveforms to the subject;
    (c) output means structured and configured to deliver an adaptive stimulation waveform or train(s) of waveforms to the subject; and
    (d) control and signal processing means structured and configured:

(1) to analyze and record the three dimensional signals being emitted by the subject's brain and received by the receiving means to determine at least one measure of brain excitability of the subject,
(2) to construct and deliver an adaptive waveform with maximal beneficial and minimal detrimental effects for treating the seizure,
(3) to adapt said adaptive waveform or train(s) of waveforms, if indicated, based on the response of the subject's brain to the delivery of a previous waveform delivered to the subject,
(4) to cause the output means to automatically deliver the desired stimulation waveform to the subject, and
(5) to continue analyzing the three dimensional signals being emitted by the subject's brain and monitored and received by the receiving means in order to assess therapeutic efficacy or safety of the desired stimulation waveform delivered to the subject.

2. A system for controlling a seizure of a subject as defined in claim 1 wherein, if the therapeutic efficacy is not statistically significant or acceptable or the safety of the desired adaptive stimulation waveform or train(s) of waveforms is determined to be not satisfactory, the control and signal processing means is further structured and configured to subsequently select and construct other desired adaptive stimulation waveforms or train(s) of waveforms from the waveform bank for automatic delivery by the output means to the subject and to assess therapeutic efficacy or safety thereof until a satisfactory or statistically significant adaptive stimulation waveform or train(s) of waveforms is delivered to the subject.

3. A system for controlling a seizure of a subject as defined in claim 1 wherein the control means is further structured and configured to cause the output means to deliver the adaptive stimulation waveform or train(s) of waveforms only once to the subject during the seizure.

4. A system for controlling a seizure of a subject as defined in claim 1 wherein the control means is further structured and configured to cause the output means to deliver the adaptive stimulation waveform or train(s) of waveforms to the subject more than once during the seizure.

5. A system for controlling a seizure of a subject as defined in claim 1 wherein the control means is further structured and configured to cause the output means to deliver the adaptive stimulation waveform or train(s) of waveforms to the subject at a selected stage of the seizure.

6. A system for controlling a seizure of a subject as defined in claim 1 wherein, if the therapeutic efficacy or safety of the desired adaptive stimulation waveform or train(s) of adaptive waveforms is determined to be ineffective or unsafe, the control and signal processing means is further structured and configured to subsequently select or construct other desired adaptive stimulation waveforms or train(s) of adaptive waveforms from the waveform bank for automatic, serial delivery by the output means to the subject and to assess therapeutic efficacy or safety thereof until an effective and safe desired adaptive stimulation waveform or train(s) of adaptive waveforms is delivered to the subject.

7. A system for controlling a seizure of a subject, the system comprising:
(a) receiving means for receiving three dimensional signals of a seizure being emitted by a subject's brain;
(b) a waveform bank containing an adaptive waveform or train(s) of adaptive waveforms;
(c) output means for three-dimensionally delivering a desired adaptive stimulation waveform or train(s) of adaptive waveforms to the subject; and
(d) control and signal processing means for:
(1) analyzing and recording the three-dimensional signals being emitted by the subject's brain and being received by the receiving means to determine at least one measure of brain excitability of the subject,
(2) determining a desired adaptive stimulation waveform or train(s) of adaptive waveforms, based on the at least one measure of brain excitability of the subject, for treating the seizure,
(3) constructing the desired adaptive stimulation waveform or train(s) of adaptive waveforms from the waveform bank,
(4) causing the output means to automatically deliver the desired adaptive stimulation waveform or train(s) of adaptive waveforms to the subject, and
(5) continuing to analyze the three-dimensional signals being emitted by the subject's brain and monitored and received by the receiving means for assessing therapeutic efficacy or safety of the desired adaptive stimulation waveform or train(s) of adaptive waveforms being delivered to the subject.

8. A system for controlling a seizure of a subject as defined in claim 7 wherein, if the therapeutic efficacy or safety of the desired adaptive stimulation waveform or train(s) of adaptive waveforms is determined to be not satisfactory or statistically not significant, the control and signal processing means also for subsequently selecting and constructing other desired adaptive stimulation waveforms or train(s) of adaptive waveforms from the waveform bank for automatic delivery by the output means to the subject and for assessing therapeutic efficacy or safety thereof until a satisfactory or statistically significant adaptive stimulation waveform or train(s) of adaptive waveforms is delivered to the subject.

9. A system for controlling a seizure of a subject as defined in claim 7 wherein, if the therapeutic efficacy or safety of the desired adaptive stimulation waveform or train(s) of adaptive waveforms is determined to be not satisfactory or statistically not significant, the control and signal processing means also for subsequently selecting or constructing other desired adaptive stimulation waveforms or train(s) of adaptive waveforms from the waveform bank for automatic delivery by the output means to the subject and for assessing therapeutic efficacy or safety thereof until a satisfactory or statistically significant adaptive stimulation waveform or train(s) of adaptive waveforms is delivered to the subject.

10. A system for controlling a seizure of a subject as defined in claim 7 wherein the control means also for causing the output means to deliver the adaptive stimulation waveform or train(s) of adaptive waveforms only once to the subject during the seizure.

11. A system for controlling a seizure of a subject as defined in claim 7 wherein the control means also causes the output means to deliver the adaptive stimulation waveform or train(s) of adaptive waveforms to the subject at a selected stage of the seizure.

* * * * *